United States Patent
Dyballa et al.

(10) Patent No.: US 9,771,311 B2
(45) Date of Patent: Sep. 26, 2017

(54) COUPLING A PHENOL AND AN ARENE USING SELENIUM DIOXIDE

(71) Applicant: Evonik Degussa GmbH, Essen (DE)

(72) Inventors: Katrin Marie Dyballa, Recklinghausen (DE); Robert Franke, Marl (DE); Dirk Fridag, Haltern am See (DE); Michael Mirion, Mainz (DE); Thomas Quell, Mainz (DE); Siegfried R. Waldvogel, Gau-Algesheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/160,367

(22) Filed: May 20, 2016

(65) Prior Publication Data
US 2016/0340281 A1    Nov. 24, 2016

(30) Foreign Application Priority Data

May 20, 2015 (EP) ..................... 15168404

(51) Int. Cl.
*C07C 41/30* (2006.01)
*C07C 43/23* (2006.01)

(52) U.S. Cl.
CPC ............. *C07C 41/30* (2013.01); *C07C 43/23* (2013.01)

(58) Field of Classification Search
None
See application file for complete search history.

(56) References Cited

U.S. PATENT DOCUMENTS

| 2015/0336865 A1 | 11/2015 | Dyballa et al. |
| 2015/0336885 A1 | 11/2015 | Dyballa et al. |
| 2015/0336995 A1 | 11/2015 | Dyballa et al. |
| 2016/0257634 A1 | 9/2016 | Dyballa et al. |
| 2016/0340304 A1 | 11/2016 | Dyballa et al. |

FOREIGN PATENT DOCUMENTS

| WO | 2005/042547 A1 | 5/2005 |
| WO | 2010/023258 A1 | 3/2010 |
| WO | 2010/139687 A1 | 12/2010 |
| WO | 2013/052585 A2 | 4/2013 |
| WO | 2015/181018 A1 | 12/2015 |
| WO | 2016/139245 A1 | 9/2016 |

OTHER PUBLICATIONS

Kirste et al. ("Efficient Anodic and Direct Phenol-Arene C,C Cross-Coupling: The Benign Role of Water of Methanol", Journal of the American Chemical Society, vol. 134., Issue 7, Jan. 2012, pp. 3571-3576).*
R. Noyori, "Centenary Lecture. Chemical multiplication of chirality: science and applications," Chem. Soc. Rev., 1989, 18: 187-208.
I. Cepanec, "Synthesis of Biaryls," Elsevier, New York, 2004, 4 pages, only Title page and Copyright page visible.
Y. Chen, S. Yekta, A. K. Yudin, "Modified BINOL Ligands in Asymmetric Catalysis," Chem. Rev. 2003, 103(8), pp. 3155-3211, only pp. 3155 and 3156 provided.
J. M. Brunel, "BINOL: A Versatile Chiral Reagent," Chem. Rev. 2005, 105(3), 857-898.
S. Kobayashi, Y. Mori, J. S. Fossey, "Catalytic Enantioselective Formation of C—C Bonds by Addition to Imines and Hydrazones: A Ten-Year Update," Chem. Rev. 2011, 111(4), 2626-2704.
G. Sartori, R. Maggi, F. Bigi, M. Grandi, "Selective synthesis of unsymmetrical hydroxylated and methoxylated biaryls," J. Org. Chem. 1993, 58(25), 7271-7273.
L. Ackermann, "Modern Arylation Methods," Wiley-VCH, Weinheim, 2009, 17 pages, Contents pp. V-XVII.
X. Chen, K. M. Engle, D.-H. Wang, J.-Q. Yu, "Palladium(II)-catalyzed C-H activation/C-C cross-coupling reactions: versatility and practicality," Angew. Chem. Int. Ed. 2009, 48(28), 5094-5115.
I. V. Seregin, V. Gevorgyan, "Direct transition metal-catalyzed functionalization of heteroaromatic compounds," Chem. Soc. Rev. 2007, 36, 1173-1193.
G. Dyker, "Handbook of C-H Transformations," Wiley-VCH, Weinheim, 2005, 26 pages, Contents pp. VII-XVII.
A. Kirste et al. "Anodic Phenol-Arene Cross-Coupling Reaction on Boron-Doped Diamond Electrodes," Angewandte Chemie International Edition, 2010; 49(5):971-5.
Paine et al. "Manganese complexes of mixed O, X, O-donor ligants (X=S or Se): synthesis, characterization and catalytic reactivity," Dalton Trans., 2003, 3136-3144.
Morimoto et al., "Metal-Free Oxidative para Cross-Coupling of Phenols," Chem. Eur. J., 2013, 19(27) pp. 8726-8731.
Parumala et al., "Reversal of Polarity in Masked o-Benzoquinones: Rapid Access to Unsymmetrical Oxygenated Biaryls," Org. Lett., 2013, 15(14), pp. 3546-3549.

* cited by examiner

*Primary Examiner* — Rosalynd Keys
(74) *Attorney, Agent, or Firm* — Michael Best & Friedrich LLP

(57) ABSTRACT

Method for coupling a phenol and an arene using selenium dioxide, and also novel phenol-arene derivatives.

14 Claims, No Drawings

COUPLING A PHENOL AND AN ARENE USING SELENIUM DIOXIDE

FIELD OF THE INVENTION

The present invention relates to a method for coupling a phenol and an arene using selenium dioxide and also novel phenol-arene derivatives.

BACKGROUND

Biaryl refers to compounds in which two aryl groups are joined to one another via a single bond. The simplest biaryl is biphenyl.

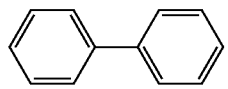 [SMILES: c1ccc(-c2ccccc2)cc1]

Scheme 1: Biphenyl as the Simplest Biaryl

Phenol-arene derivatives are compounds in which one aryl unit bears an OH group ("phenol") and the other aryl unit ("arene") bears no free OH groups. Alkoxy groups, i.e. protected OH groups, on the arene ring are permitted however.

Biphenols and biaryls serve as synthesis units for catalytically active substances and are therefore of industrial interest. Biaryls are important units for liquid crystals, organic devices, dyes, ligands for metal catalysts, and find uses even in medical areas, since these structures are ubiquitous in biologically active, naturally occurring products (cf. a) R. Noyori, Chem. Soc. Rev. 1989, 18, 187; b) I. Cepanec, Synthesis of Biaryls, Elsevier, New York, 2004). The 2,2'-biphenols in particular can be used for this purpose (cf. WO 2005/042547). These are employed particularly as ligand components for catalysts. In this case, the biphenol can be used, for example, as ligand unit in the enantioselective catalysis (cf. Y. Chen, S. Yekta, A. K. Yudin, Chem. Rev. 2003, 103, 3155-3211; J. M. Brunel Chem. Rev. 2005, 105, 857-898; S. Kobayashi, Y. Mori, J. S. Fossey, Chem. Rev. 2011, 11, 2626-2704).

Direct coupling of unprotected phenol derivatives under conventional organic conditions has been possible only in a few examples to date. For this purpose, usually superstoichiometric amounts of inorganic oxidizing agents such as $AlCl_3$, $FeCl_3$, $MnO_2$, or 2,3-dichloro-5,6-dicyano-1,4-benzoquinone, which is organic, have been used (cf. G. Sartori, R. Maggi, F. Bigi, M. Grandi, J. Org. Chem. 1993, 58, 7271).

Alternatively, such coupling reactions are conducted in a multistage sequence. In this case, leaving functionalities and often toxic, complicated transition metal catalysts based on palladium, for example, are used (cf. L. Ackermann, Modern Arylation Methods, Wiley-VCH, Weinheim, 2009, X. Chen, K. M. Engle, D.-H. Wang, J.-Q. Yu, Angew. Chem. Int. Ed. 2009, 48, 5094-511, I. V. Seregin, V. Gevorgyan, Chem. Soc. Rev. 2007, 36, 1173-1193, G. Dyker, Handbook of C—H Transformations, Wiley-VCH, Weinheim, 2005).

A great disadvantage of the abovementioned methods for phenol coupling is the need to operate in anhydrous solvents with exclusion of air. Superstoichiometric amounts of the relevant oxidizing agent are frequently required. The scarcity of raw materials (e.g. boron and bromine) leads to rising prices which leads to uneconomical processes. Multi-stage syntheses require the use of different solvents and multiple purification up to attainment of the desired product.

One possible way of synthesizing these biphenols is by means of electrochemical processes. In this context, carbon electrodes such as graphite, glassy carbon, boron-doped diamond (BDD) or noble metals such as platinum were used; cf. WO2010139687A1 and WO2010023258A1. A disadvantage of these electrochemical methods is the cost of some of the apparatus, which has to be manufactured specially. Moreover, scale-up to the ton scale, as is typically required in industry, is sometimes very complex and in some cases even impossible. In particular, scale-up of the electrode materials (BDD) is currently still not possible.

Furthermore, the preparation by electrochemical methods requires the use of sometimes costly conductive salts, the reusability of which cannot be ensured. The technical complexity of electrochemical reactions is also immense. Therefore, the preparation of large electrode surfaces of BDD is only possible to a limited extent and is linked with high costs. Even small defects in BDD surfaces moreover can lead to a complete destruction of the electrodes.

The coupling of arenes and phenols to give the corresponding phenol-arene derivatives is a great challenge just like the coupling of arenes or phenols to give the corresponding biaryl or biphenol derivatives, respectively, since these reactions are often neither regioselective nor chemoselective.

SUMMARY OF THE INVENTION

An object of the following invention consisted of providing methods in which phenols and arenes can be coupled to each other without electrochemical methods being necessary and without having to work with bromine- or boron-containing leaving functionalities on the OH groups.

DETAILED DESCRIPTION

The object is achieved by a method according to claim 1.

Method for preparing phenol-arene derivatives, comprising the method steps of:
a) adding a phenol to the reaction mixture,
b) adding an arene from the group of mono- and bicyclic arenes,
c) adding selenium dioxide to the reaction mixture,
d) adding a solvent,
e) heating the reaction mixture so that the substituted phenol and the arene, from the group of mono- or bicyclic arenes, are converted to a phenol-arene derivative.

The sequence in which the phenol, the arene and the selenium dioxide are added to the reaction mixture is unimportant. In principle, further components may also be present in the reaction mixture, for example solvent or acid.

In the context of the present invention, the term arene unit is understood to mean, besides unsubstituted aryl and phenyl, also a substituted aryl such as phenyl and also naphthyl. The generic term aryls and phenols should be understood in this connection to mean both unsubstituted and substituted compounds, as discussed further below. Substitution here is on the benzene ring.

In the context of the present invention, the term "solvent" is understood to mean compounds from the solvent group of tetrahydrofuran, ethylene glycol dimethyl ether, bis(2-methoxyethyl) ether, diethyl ether, toluene, halogenated solvents or halogenated or non-halogenated acids.

The purpose of the solvent is to ensure dissolution, mixing and stirrability of the different components with one another.

In one variant of the method, the phenol is a compound of the general formula (I):

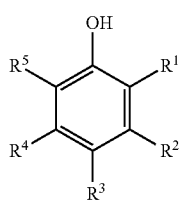

where $R^1$, $R^2$, $R^3$, $R^4$, $R^5$ are each independently selected from:

—H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, where the alkyl and aryl groups mentioned may be substituted, and at least one of the $R^1$ or $R^5$ or $R^2$ or $R^4$ radicals is —H, and the monocyclic arene is a compound of the general formula (II):

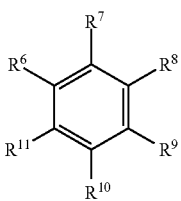

—H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, where the alkyl and aryl groups mentioned may be substituted, and at least one of the $R^6$, $R^7$, $R^8$, $R^9$, $R^{10}$ or $R^{11}$ radicals is —H.

In one variant of the method, $R^1$, $R^2$, $R^3$, $R^4$, $R^5$, $R^6$, $R^7$, $R^8$, $R^9$, $R^{10}$, $R^{11}$ are each independently selected from:

—H, —$(C_1$-$C_{12})$-alkyl, —O—$(C_1$-$C_{12})$-alkyl, —$(C_6$-$C_{20})$-aryl, —O—$(C_6$-$C_{20})$-aryl, —Cl, where the alkyl and aryl groups mentioned may be substituted, and at least one of the $R^6$, $R^7$, $R^8$, $R^9$, $R^{10}$, $R^{11}$ radicals is —H.

In one variant of the method, $R^1$, $R^2$, $R^3$, $R^4$, $R^5$, $R^6$, $R^7$, $R^8$, $R^9$, $R^{10}$, $R^{11}$ are each independently selected from:

—H, —$(C_1$-$C_{12})$-alkyl, —O—$(C_1$-$C_{12})$-alkyl, —$(C_6$-$C_{20})$-aryl, —Cl, where the alkyl and aryl groups mentioned may be substituted, and at least one $R^6$, $R^7$, $R^8$, $R^9$, $R^{10}$, $R^{11}$ radical is —H.

In one variant of the method, the $R^1$, $R^2$, $R^3$, $R^4$, $R^5$, $R^6$, $R^7$, $R^8$, $R^9$, $R^{10}$, $R^{11}$ radicals are each independently selected from:

—H, —$(C_1$-$C_{12})$-alkyl, —O—$(C_1$-$C_{12})$-alkyl, —Cl, and at least one of the $R^1$, $R^5$, $R^2$, $R^3$ radicals is —H, and at least one of the $R^6$, $R^7$, $R^8$, $R^9$, $R^{10}$, $R^{11}$ radicals is —H, where the alkyl groups mentioned may be substituted.

In one variant of the method, the $R^1$, $R^2$, $R^3$, $R^4$, $R^5$, $R^6$, $R^7$, $R^8$, $R^9$, $R^{10}$, $R^{11}$ radicals are each independently selected from:

—H, —$(C_1$-$C_{12})$-alkyl, —O—$(C_1$-$C_{12})$-alkyl, and at least one of the $R^1$, $R^5$, $R^2$, $R^3$ radicals is —H, and at least one of the $R^6$, $R^7$, $R^8$, $R^9$, $R^{10}$, $R^{11}$ radicals is —H, where the alkyl groups mentioned may be substituted.

In one variant of the method, the phenol is a compound of the general formula (I):

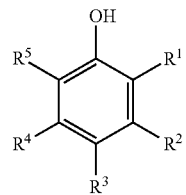

where $R^1$, $R^2$, $R^3$, $R^4$, $R^5$ are each independently selected from:

—H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, where the alkyl and aryl groups mentioned may be substituted, and at least one of the $R^1$ or $R^5$ or $R^2$ or $R^4$ radicals is —H, and the bicyclic arene is a compound of the general formula (III):

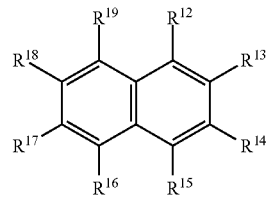

where $R^{12}$, $R^{13}$, $R^{14}$, $R^{15}$, $R^{16}$, $R^{17}$, $R^{18}$, $R^{19}$ are each independently selected from:

—H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen, and at least one of the $R^{12}$, $R^{13}$, $R^{14}$, $R^{15}$, $R^{16}$, $R^{17}$, $R^{18}$ or $R^{19}$ radicals is —H, where the alkyl groups mentioned may be substituted.

$(C_1$-$C_{12})$-Alkyl and O—$(C_1$-$C_{12})$-alkyl may each be unsubstituted or substituted by one or more identical or different radicals selected from $(C_3$-$C_{12})$-cycloalkyl, $(C_3$-$C_{12})$-heterocycloalkyl, $(C_6$-$C_{20})$-aryl, fluorine, chlorine, cyano, formyl, acyl and alkoxycarbonyl.

$(C_6$-$C_{20})$-Aryl and —$(C_6$-$C_{20})$-aryl-$(C_6$-$C_{20})$-aryl- may each be unsubstituted or substituted by one or more identical or different radicals selected from —H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen (such as Cl, F, Br, I), —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, —N[$(C_1$-$C_{12})$-alkyl]$_2$.

In the context of the invention, the expression "—$(C_1$-$C_{12})$-alkyl" encompasses straight-chain and branched alkyl groups. Preferably, these groups are unsubstituted straight-chain or branched —$(C_1$-$C_8)$-alkyl groups and most preferably —$(C_1$-$C_6)$-alkyl groups. Examples of —$(C_1$-$C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—$(C_1\text{-}C_{12})$-alkyl" also apply to the alkyl groups in —O—$(C_1\text{-}C_{12})$-alkyl, i.e. in —$(C_1\text{-}C_{12})$-alkoxy. Preferably, these groups are unsubstituted straight-chain or branched —$(C_1\text{-}C_6)$-alkoxy groups.

Substituted —$(C_1\text{-}C_{12})$-alkyl groups and substituted —$(C_1\text{-}C_{12})$-alkoxy groups may have one or more substituents, depending on their chain length. The substituents are preferably independently selected from —$(C_3\text{-}C_{12})$-cycloalkyl, —$(C_3\text{-}C_{12})$-heterocycloalkyl, —$(C_6\text{-}C_{20})$-aryl, fluorine, chlorine, cyano, formyl, acyl and alkoxycarbonyl.

The expression "—$(C_3\text{-}C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl.

One example of a substituted cycloalkyl would be menthyl.

The expression "—$(C_3\text{-}C_{12})$-heterocycloalkyl groups", in the context of the present invention, encompasses nonaromatic, saturated or partly unsaturated cycloaliphatic groups having 3 to 12, especially 5 to 12, carbon atoms. The —$(C_3\text{-}C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3\text{-}C_{12})$-heterocycloalkyl groups are tetrahydrothiophenyl, tetrahydrofuryl, tetrahydropyranyl, menthyl and dioxanyl.

In the context of the present invention, the expression "—$(C_6\text{-}C_{20})$-aryl" and "—$(C_6\text{-}C_{20})$-aryl-$(C_6\text{-}C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6\text{-}C_{10})$-aryl and —$(C_6\text{-}C_{10})$-aryl-$(C_6\text{-}C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6\text{-}C_{20})$-aryl groups and —$(C_6\text{-}C_{20})$-aryl-$(C_6\text{-}C_{20})$-aryl groups may have one or more (e.g. 1, 2, 3, 4 or 5) substituents, depending on the ring size. These substituents are preferably independently selected from —H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl, -halogen (such as Cl, F, Br, I), —COO—$(C_1\text{-}C_{12})$-alkyl, —CONH—$(C_1\text{-}C_{12})$-alkyl, —$(C_6\text{-}C_{20})$-aryl-CON[$(C_1\text{-}C_{12})$-alkyl]$_2$, —CO—$(C_1\text{-}C_{12})$-alkyl, —CO—$(C_6\text{-}C_{20})$-aryl, —COOH, —OH, —SO$_3$H, —SO$_3$Na, —NO$_2$, —CN, —NH$_2$, —N[$(C_1\text{-}C_{12})$-alkyl]$_2$.

Substituted —$(C_6\text{-}C_{20})$-aryl groups and —$(C_6\text{-}C_{20})$-aryl-$(C_6\text{-}C_{20})$-aryl groups are preferably substituted —$(C_6\text{-}C_{10})$-aryl groups and —$(C_6\text{-}C_{10})$-aryl-$(C_6\text{-}C_{10})$-aryl groups, especially substituted phenyl or substituted naphthyl or substituted anthracenyl. Substituted —$(C_6\text{-}C_{20})$-aryl groups preferably bear one or more, for example 1, 2, 3, 4 or 5, substituents selected from —$(C_1\text{-}C_{12})$-alkyl groups, —$(C_1\text{-}C_{12})$-alkoxy groups.

In one variant of the method, $R^1$, $R^2$, $R^3$, $R^4$, $R^5$ are each independently selected from:
—H, —$(C_1\text{-}C_{12})$-alkyl, —O—$(C_1\text{-}C_{12})$-alkyl, —$(C_6\text{-}C_{20})$-aryl, —O—$(C_6\text{-}C_{20})$-aryl, —Cl,
where the alkyl and aryl groups mentioned may be substituted,
and at least one of the $R^1$ or $R^5$ or $R^2$ or $R^4$ radicals is —H, and the bicyclic arene is preferably a compound of the general formula (III), where $R^{12}$, $R^{13}$, $R^{14}$, $R^{15}$, $R^{16}$, $R^{17}$, $R^{18}$, $R^{19}$ are each independently selected from:
—H, —$(C_1\text{-}C_{12})$-alkyl, —O—$(C_1\text{-}C_{12})$-alkyl, —$(C_6\text{-}C_{20})$-aryl, —O—$(C_6\text{-}C_{20})$-aryl, —Cl,
where the alkyl and aryl groups mentioned may be substituted,
and at least one $R^{12}$, $R^{13}$, $R^{14}$, $R^{15}$, $R^{16}$, $R^{17}$, $R^{18}$ or $R^{19}$ radical is —H.

In one variant of the method, the $R^1$, $R^2$, $R^3$, $R^4$, $R^5$, $R^{12}$, $R^{13}$, $R^{14}$, $R^{15}$, $R^{16}$, $R^{17}$, $R^{18}$, $R^{19}$ radicals are each independently selected from:
—H, —$(C_1\text{-}C_{12})$-alkyl, —O—$(C_1\text{-}C_{12})$-alkyl, —Cl,
where the alkyl groups mentioned may be substituted,
and at least one of the $R^1$ or $R^5$ or $R^2$ or $R^3$ radicals is —H, and at least one of the $R_{12}$, $R_{13}$, $R_{14}$, $R_{15}$, $R_{16}$, $R_{17}$, $R_{18}$ or $R_{19}$ radicals is —H.

In one variant of the method, the $R^1$, $R^2$, $R^3$, $R^4$, $R^5$, $R^{12}$, $R^{13}$, $R^{14}$, $R^{15}$, $R^{16}$, $R^{17}$, $R^{18}$, $R^{19}$ radicals are each independently selected from:
—H, —$(C_1\text{-}C_{12})$-alkyl, —O—$(C_1\text{-}C_{12})$-alkyl,
where the alkyl groups mentioned may be substituted,
and at least one of the $R^1$ or $R^5$ or $R^2$ or $R^3$ radicals is —H, and at least one of the $R^{12}$, $R^{13}$, $R^{14}$, $R^{15}$, $R^{16}$, $R^{17}$, $R^{18}$ or $R^{19}$ radicals is —H.

If a monocyclic arene is used in the method according to the invention, the monocyclic arene is preferably a phenyl derivative.

If a bicyclic arene is used in the method according to the invention, the bicyclic arene is preferably a naphthyl derivative.

In addition to the phenol, the arene and the selenium dioxide, the reaction mixture can also include a solvent, such as tetrahydrofuran, ethylene glycol dimethyl ether, bis(2-methoxyethyl) ether, diethyl ether, toluene, fluorinated solvents or organic acids. By addition of the solvent, an improvement is achieved in dissolution, mixing and/or stirrability of the different components with one another.

In one variant of the method according to the invention, a fluorinated solvent is added. In a preferred embodiment of the method according to the invention, a carboxylic acid, preferably formic acid, is added.

In a further preferred embodiment of the method according to the invention, a fluorinated carboxylic acid or a fluorinated alcohol is added as solvent.

In a particularly preferred embodiment of the method according to the invention, trifluoroacetic acid or 1,1,1,3,3,3-hexafluoro-2-propanol and especially preferably 1,1,1,3,3,3-hexafluoro-2-propanol is added as solvent.

A particular advantage of the reaction systems described here is that they are not susceptible to moist ambient air, i.e. a mixture of water vapour, oxygen and nitrogen. Consequently, there is no need to work with exclusion of air, which considerably simplifies the implementation of the reaction and then makes it industrially practicable. The option of conducting the process in the presence of moist air is therefore of particular interest.

In the method according to the invention, the selenium dioxide is added in a molar ratio, based on the sum total of the phenol and the arene, preferably within a range from 0.1 to 2.0. Preference is given here to the range from 0.25 to 1.5, and particular preference to the range from 0.4 to 1.2.

The fact that the selenium dioxide can be used in a substoichiometric amount is a further advantage over the reaction described in the prior art with other inorganic oxidizing agents, for example $AlCl_3$, $FeCl_3$ or $MnO_2$.

In the method according to the invention, the reaction mixture is heated to a temperature in the range from 25° C. to 120° C., preferably 30° C. to 100° C. and particularly preferably 30° C. to 60° C.

The temperatures specified here are the temperatures measured in the oil bath. The heating may be effected over a period in the range from 5 minutes to 24 hours. Preference is given to 15 minutes to 12 hours and particular preference to 15 minutes to 2.0 hours.

In addition to the method, inventive mono- and bicyclic arene-phenol derivatives of the formulae 2, 3, 4 and 5 are claimed:

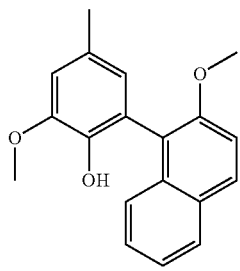

(2)

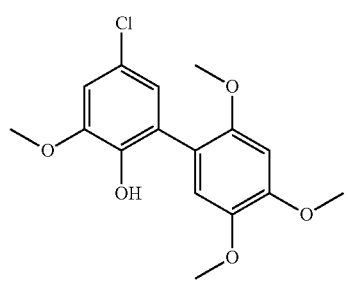

(3)

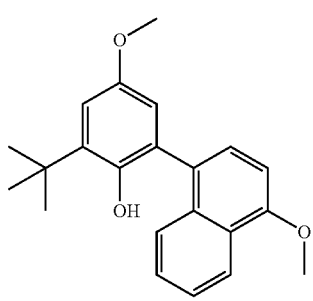

(4)

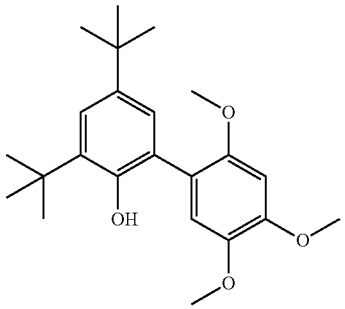

(5)

The invention is further illustrated in detail below by working examples without being limited thereto.

Analysis

Chromatography

The preparative liquid chromatography separations via "flash chromatography" were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-layer chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulphate tetrahydrate and 13.3 g of concentrated sulphuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectra (GCMS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GCMS: ion source temperature: 200° C.).

Mass Spectrometry

All electrospray ionization analyses (ESI+) were conducted on a QTof Ultima 3 from Waters Micromasses, Milford, Mass. EI mass spectra and the high-resolution EI spectra were analysed on an instrument of the MAT 95 XL sector field instrument type from Thermo Finnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The $^1$H and $^{13}$C spectra were calibrated according to the residual content of undeuterated solvent using the NMR Solvent Data Chart from Cambridge Isotopes Laboratories, USA. Some of the $^1$H and $^{13}$C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which need not correspond to IUPAC nomenclature.

EXAMPLES

General Procedures

GP1: Procedure for Coupling by Selenium Dioxide

One equivalent of phenol component A was dissolved with one equivalent of phenol/arene component B in 4-6 mL of 1,1,1,3,3,3-hexafluoroisopropanol and the mixture treated with 0.5 equivalents of selenium dioxide. The mixture was heated to boiling with stirring. After a reaction time of 60-75 minutes, the reaction solution was filtered, diluted with ethyl acetate and washed with water. The organic phase was separated, dried over magnesium sulphate and the solvent removed by distillation under reduced pressure. The crude product thus obtained was purified by column chromatography on silica gel 60.

Example 1

2-Hydroxy-2',3,4',5'-tetramethoxy-5-methylbiphenyl (1)

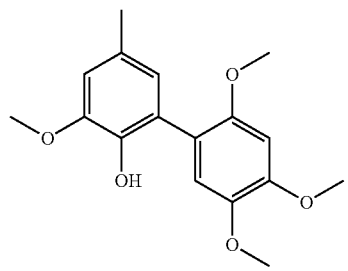

(1)

The reaction was carried out according to GP1 with 200 mg (1.45 mmol, 1.0 eq.) of 4-methylguaiacol and 243 mg (1.45 mmol, 1.0 eq.) of 1,2,4-trimethoxybenzene in 4 mL of HFIP and with addition of 80 mg (0.72 mmol, 0.5 eq.) of selenium dioxide. The reaction time was one hour. After extraction and removal of the solvent, the product mixture obtained was purified by means of column chromatography on silica gel 60 using 5:1 (cy:EE) as eluent. The product was obtained as a pale yellow, highly viscous oil.

Yield: 139 mg (0.45 mmol, 32%)

$^1$H-NMR (400 MHz, CDCl$_3$): δ [ppm]=2.33 (s, 3H), 3.81 (s, 3H) 3.86 (s, 3H), 3.91 (s, 3H), 3.94 (s, 3H), 5.98 (bs, 1H), 6.65 (s, 1H), 6.69 (s, 1H), 6.71 (s, 1H), 6.85 (s, 1H)
$^{13}$C-NMR (101 MHz, CDCl$_3$): δ [ppm]=21.32, 5615, 56.29, 56.60, 57.44, 98.56, 111.37, 115.12, 118.70, 123.53, 125.34, 129.03, 141.02, 143.73, 147.89, 149.71, 150.47
HRMS (ESI, pos.mode): m/z [M+Na$^+$]: calculated: 327.1208. found: 327.1212.

Example 2

1-(2-Hydroxy-3-methoxy-5-methylphenyl)-2-methoxynaphthalene (2)

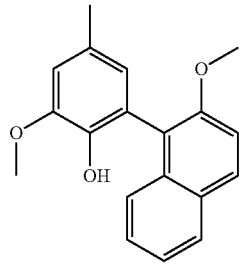

(2)

The reaction was carried out according to GP1 with 200 mg (1.45 mmol, 1.0 eq.) of 4-methylguaiacol and 343 mg (2.17 mmol, 1.5 eq.) of 1-methoxynaphthalene in 5 mL of HFIP and with addition of 96 mg (0.87 mmol, 0.6 eq.) of selenium dioxide. The reaction time was 75 minutes. After extraction and removal of the solvent, the product mixture obtained was purified by means of column chromatography on silica gel 60 using 95:5 (cy:EE) as eluent. The product was obtained as a yellow highly viscous oil.

Yield: 45 mg, (0.15 mmol, 11%)
$^1$H-NMR (400 MHz, CDCl$_3$): δ [ppm]=2.36 (s, 3H), 3.89 (s, 3H), 3.95 (s, 3H), 5.37 (bs, 1H), 6.65 (s, 1H), 6.79 (s, 1H), 7.33-7.36 (m, 2H), 7.40 (d, 1H, J=12 Hz), 7.46-7.49 (m, 1H), 7.81-7.84 (m, 1H), 7.91 (d, 1H, J=12 Hz).
$^{13}$C-NMR (101 MHz, CDCl$_3$): δ [ppm]=21.39, 56.05, 57.11, 111.24, 113.96, 120.50, 122.21, 123.69, 124.46, 125.35, 126.50, 128.01, 129.10, 129.28, 129.60, 133.62, 141.51, 146.67, 154.89.
HRMS (ESI, pos.mode): m/z for C$_{19}$H$_{20}$O$_3$[M+H$^+$]: calculated: 295.1333. found: 295.1334.

Example 3

5-Chloro-2-hydroxy-2',3,3',6'-tetramethoxybiphenyl (3)

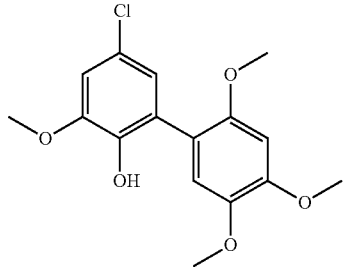

(3)

The reaction was carried out according to GP1 with 400 mg (2.52 mmol, 2.0 eq.) of 4-chloro-2-methoxyphenol and 313 mg (1.86 mmol, 1.0 eq.) of 1,2,4-trimethoxybenzene in 8 mL of HFIP and with addition of 161 mg (1.45 mmol, 0.5 eq.) of selenium dioxide. The reaction time was 75 minutes. After extraction and removal of the solvent, the product mixture obtained was purified by means of column chromatography on silica gel 60 using 5:1 (cy:EE) as eluent. The product was obtained as a brown highly viscous oil.

Yield: 181 mg (0.56 mmol, 30%)

$^1$H-NMR (400 MHz, CDCl$_3$): δ [ppm]=3.81 (s, 3H), 3.86 (s, 3H), 3.91 (s, 3H), 3.94 (s, 1H), 6.10 (bs, 1H), 6.64 (s, 1H), 6.82 (s, 1H), 6.85 (d, 1H, J=4 Hz), 6.88 (d, 1H, J=4 Hz).

$^{13}$C-NMR (101 MHz, CDCl$_3$): δ [ppm]=56.27, 56.40, 56.61, 57.42, 98.44, 110.79, 114.79, 117.19, 122.88, 124.55, 126.49, 142.07, 143.80, 148.29, 149.81, 150.40.

HRMS (ESI, pos.mode): m/z for C$_{16}$H$_{17}$O$_5$Cl [M+Na$^+$]: calculated: 347.0662. found: 347.0663.

Example 4

4-(3-tert-Butyl-2-hydroxy-5-methoxyphenyl)-1-methoxynaphthalene (4)

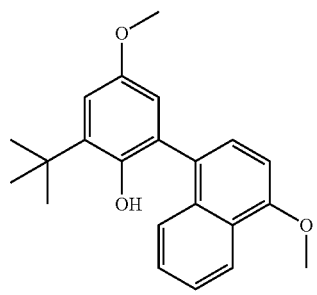

(4)

The reaction was carried out according to GP1 with 300 mg (1.66 mmol, 1.0 eq.) of 4-methoxy-2-tert-butylphenol and 263 mg (1.66 mmol, 1.0 eq.) of 1-methoxynaphthalene in 4.6 mL of HFIP and with addition of 92 mg (0.83 mmol, 0.5 eq.) of selenium dioxide. The reaction time was one hour. After extraction and removal of the solvent, the product mixture obtained was purified by means of column chromatography on silica gel 60 using 95:5 (cy:EE) as eluent. The product was obtained as an orange-brown highly viscous oil.

Yield: 135 mg (0.4 mmol, 24%)

$^1$H-NMR (400 MHz, CDCl$_3$): δ [ppm]=1.47 (s, 9H), 3.76 (s, 3H), 3.91 (s, 3H), 4.78 (bs, 1H), 6.61 (d, 1H, J=4 Hz), 7.01 (d, 1H, J=4 Hz), 7.38-7.42 (m, 3H), 7.50-7.52 (m, 1H), 7.84-7.87 (m, 1H), 7.6 (d, 1H, J=8 Hz).

$^{13}$C-NMR (101 MHz, CDCl$_3$): δ [ppm]=29.69, 35.21, 55.73, 56.91, 112.90, 113.74, 114.16, 119.07, 123.23, 124.19, 125.20, 127.22, 128.15, 129.49, 130.61, 133.85, 137.92, 146.54, 152.58, 154.72.

Example 5

3,5-Di-tert-butyl-2-hydroxy-2',4',5'-trimethoxybiphenyl (5)

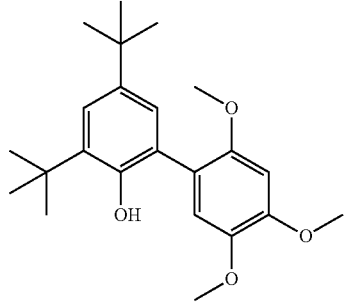

(5)

In a 50 mL round-bottom flask, 0.90 g of 2,4-di-tert-butylphenol (4.3 mmol) were dissolved with 3.63 g of 1,2,4-trimethoxybenzene (21.6 mmol) in 35 mL of hexafluoroisopropanol and the mixture heated in a warm oil bath at 55° C. After 10 minutes, 0.48 g of selenium dioxide (4.3 mmol) were added. After 170 minutes, the reaction was terminated by addition of 8 mL of water and the hexafluoroisopropanol was distilled off under reduced pressure. The residue was taken up in 60 mL of ethyl acetate and washed twice with saturated sodium chloride solution. The organic phase was separated, dried over magnesium sulphate and the solvent distilled under reduced pressure. Excess 1,2,4-trimethoxybenzene was removed in a Kugelrohr oven (80° C., 1*10$^{-3}$ mbar). The crude product was purified by column chromatography. In this case, an automated column system from BÜCHI-Labortechnik GmbH, Essen was used. The column length was 32 cm and the diameter 6 cm. The eluent used was cyclohexane/ethyl acetate, operating with an ethyl acetate gradient of: 0% (over 5 min), 0-3% (over 4 min), 3-6% (over 8 min), 6-12% (over 8 min), 12-24% (over 8 min), 24-48% (over 8 min), 48-100% (over 8 min). The pumping rate was 100 mL/min.

Yield: 0.727 g (1.9 mmol), 45%

GC: t$_R$(hard method, HP-5)=15.076 min $^1$H-NMR: (400 MHz, CDCl$_3$) δ [ppm]=1.35 (s, 9H), 1.48 (s, 9H), 3.84 (s, 3H), 3.88 (s, 3H), 3.96 (s, 3H), 6.20 (s, 1H), 6.67 (s, 1H), 6.88 (s, 1H), 7.12 (d, J=2.5 Hz, 1H), 7.37 (d, J=2.5 Hz, 1H).

$^{13}$C-NMR: 29.98, 31.82, 34.49, 35.35, 56.38, 56.71, 57.35, 98.38, 116.06, 119.45, 123.72, 125.88, 126.14, 136.67, 142.34, 144.27, 149.64, 149.97, 150.11.

Example 6

5,6-Dimethyl-2-hydroxy-2',3,3',4'-tetramethoxybiphenyl (6)

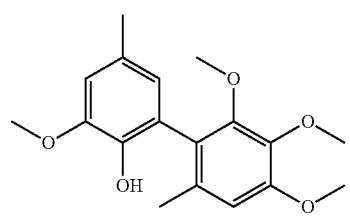

(6)

In a 50 mL round-bottom flask, 0.60 g of 4-methylguaiacol (4.3 mmol) were dissolved with 6.04 g of 3,4,5- trimethoxytoluene (21.7 mmol) in 36 mL of hexafluoroisopropanol and the mixture heated in a warm oil bath at 55° C. After 10 minutes, 0.48 g of selenium dioxide (4.3 mmol) were added. After 180 minutes, the reaction was terminated by addition of 8 mL of water and the hexafluoroisopropanol was distilled off under reduced pressure. The residue was taken up in 60 mL of ethyl acetate and washed twice with saturated sodium chloride solution. The organic phase was separated, dried over magnesium sulphate and the solvent distilled under reduced pressure. Excess 3,4,5-trimethoxytoluene was removed in a Kugelrohr oven (80° C., 1*10$^{-3}$ mbar). The crude product was purified by column chromatography. In this case, an automated column system from BÜCHI-Labortechnik GmbH, Essen was used. The column length was 32 cm and the diameter 6 cm. The eluent used was cyclohexane/ethyl acetate, operating with an ethyl acetate gradient of: 0% (over 5 min), 0-3% (over 4 min), 3-6% (over 8 min), 6-12% (over 8 min), 12-24% (over 8 min), 24-48% (over 8 min), 48-100% (over 8 min). The pumping rate was 100 mL/min.

Yield: 0.586 g (1.8 mmol), 42%

GC: $t_R$(hard method, HP-5)=13.925 min $^1$H-NMR: (400 MHz, CDCl$_3$) δ [ppm]=2.06 (s, 3H), 2.32 (s, 3H), 3.68 (s, 3H), 3.89 (s, 3H), 3.91 (s, 3H), 5.44 (s, 1H), 6.52 (d, J=1.7 Hz, 1H), 6.62 (s, 1H), 6.69 (d, J=1.7 Hz, 1H).

$^{13}$C-NMR: 20.19, 21.34, 55.97, 56.01, 61.04, 61.15, 109.04, 110.78, 123.24, 123.77, 124.03, 128.83, 132.84, 140.19, 140.86, 146.49, 151.77, 152.64.z

HRMS (ESI, pos.mode): m/z for [M+Na$^+$]: calculated: 341.1365. found: 341.1376.

The results show that the method according to the invention is a synthesis route with which coupled phenol-arene derivatives may be selectively prepared.

The invention claimed is:

1. Method for preparing phenol-arene derivatives, comprising the method steps of:
   a) adding a phenol to the reaction mixture,
   b) adding an arene from the group of mono- and bicyclic arenes,
   c) adding selenium dioxide to the reaction mixture,
   d) adding a solvent,
   e) heating the reaction mixture so that the substituted phenol and the arene, from
   f) the group of mono- or bicyclic arenes, are converted to a phenol-arene derivative.

2. Method according to claim 1,
wherein the phenol is a compound of the general formula (I):

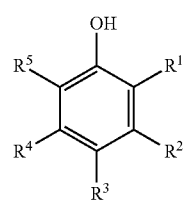

where $R^1$, $R^2$, $R^3$, $R^4$, $R^5$ are each independently selected from:
—H, —(C$_1$-C$_{12}$)-alkyl, —O—(C$_1$-C$_{12}$)-alkyl, —(C$_6$-C$_{20}$)-aryl, —O—(C$_6$-C$_{20}$)-aryl, -halogen,
where the alkyl and aryl groups mentioned may be substituted,
and at least $R^1$ or $R^5$ or $R^2$ or $R^4$ is —H,
and the monocyclic arene is a compound of the general formula (II):

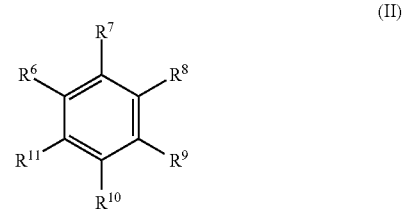

where $R^6$, $R^7$, $R^8$, $R^9$, $R^{10}$, $R^{11}$ are each independently selected from:
—H, —(C$_1$-C$_{12}$)-alkyl, —O—(C$_1$-C$_{12}$)-alkyl, —(C$_6$-C$_{20}$)-aryl, —O—(C$_6$-C$_{20}$)-aryl, -halogen,
where the alkyl and aryl groups mentioned may be substituted,
and at least one of the $R^6$, $R^7$, $R^8$, $R^9$, $R^{19}$ or $R^{11}$ radicals is —H.

3. Method according to claim 2,
wherein $R^1$, $R^2$, $R^3$, $R^4$, $R^5$, $R^6$, $R^7$, $R^8$, $R^9$, $R^{10}$, $R^{11}$ are each independently selected from:
—H, —(C$_1$-C$_{12}$)-alkyl, —O—(C$_1$-C$_{12}$)-alkyl, —(C$_6$-C$_{20}$)-aryl, —O—(C$_6$-C$_{20}$)-aryl,
where the alkyl and aryl groups mentioned may be substituted,
and at least one of the $R^6$, $R^7$, $R^8$, $R^9$, $R^{10}$, $R^{11}$ radicals is —H.

4. Method according to claim 2,
wherein $R^1$, $R^2$, $R^3$, $R^4$, $R^5$, $R^6$, $R^7$, $R^8$, $R^9$, $R^{10}$, $R^{11}$ are each independently selected from:
—H, —(C$_1$-C$_{12}$)-alkyl, —O—(C$_1$-C$_{12}$)-alkyl, —(C$_6$-C$_{20}$)-aryl,
where the alkyl and aryl groups mentioned may be substituted,
and at least one $R^6$, $R^7$, $R^8$, $R^9$, $R^{10}$, $R^{11}$ radical is —H.

5. Method according to claim 2,
wherein the $R^1$, $R^2$, $R^3$, $R^4$, $R^5$, $R^6$, $R^7$, $R^8$, $R^9$, $R^{10}$, $R^{11}$ radicals are each independently selected from:
—H, —(C$_1$-C$_{12}$)-alkyl, —O—(C$_1$-C$_{12}$)-alkyl,
and at least one of the $R^1$, $R^5$, $R^2$, $R^3$ radicals is —H,
and at least one of the $R^6$, $R^7$, $R^8$, $R^9$, $R^{10}$, $R^{11}$ radicals is —H,
where the alkyl groups mentioned may be substituted.

6. Method according to claim 2,
wherein the $R^1$, $R^2$, $R^3$, $R^4$, $R^5$, $R^6$, $R^7$, $R^8$, $R^9$, $R^{10}$, $R^{11}$ radicals are each independently selected from:
—H, —(C$_1$-C$_{12}$)-alkyl, —O—(C$_1$-C$_{12}$)-alkyl,
and at least one of the $R^1$, $R^5$, $R^2$, $R^3$ radicals is —H,
and at least one of the $R^6$, $R^7$, $R^8$, $R^9$, $R^{10}$, $R^{11}$ radicals is —H,
where the alkyl groups mentioned may be substituted.

7. Method according to claim 1,
wherein the phenol is a compound of the general formula (I):

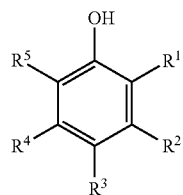

(I)

where $R^1$, $R^2$, $R^3$, $R^4$, $R^5$ are each independently selected from:
—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen,
where the alkyl and aryl groups mentioned may be substituted,
and at least one of the $R^1$ or $R^5$ or $R^2$ or $R^4$ radicals is —H,
and the bicyclic arene is a compound of the general formula (III):

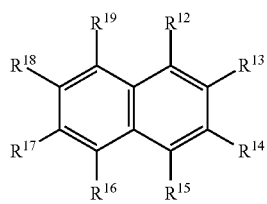

(III)

where $R^{12}$, $R^{13}$, $R^{14}$, $R^1$s, $R^{16}$, $R^{17}$, $R^{18}$, $R^{19}$ are each independently selected from:
—H, —($C_1$-$C_{12}$)-alkyl, —O—($C_1$-$C_{12}$)-alkyl, —($C_6$-$C_{20}$-aryl, —O—($C_6$-$C_{20}$-aryl, -halogen,
and at least one of the $R^{12}$, $R^{13}$, $R^{14}$, $R^{15}$, $R^{16}$, $R^{17}$, $R^{18}$ or $R^{19}$ radicals is —H,
where the alkyl groups mentioned may be substituted.

8. Method according to claim 7,
where $R^1$, $R^2$, $R^3$, $R^4$, $R^5$ are each independently selected from:
—H, —($C_1$-$C_{12}$)-alkyl, —O—($C_1$-$C_{12}$)-alkyl, —($C_6$-$C_{20}$)-aryl, —O—($C_6$-$C_{20}$)-aryl, —Cl,
where the alkyl and aryl groups mentioned may be substituted,
and at least one of the $R^1$ or $R^5$ or $R^2$ or $R^4$ radicals is —H,
and the bicyclic arene is preferably a compound of the general formula (III), where $R^{12}$, $R^{13}$, $R^{14}$, $R^{15}$, $R^{16}$, $R^{17}$, $R^{18}$, $R^{19}$ are each independently selected from:
—H, —($C_1$-$C_{12}$)-alkyl, —O—($C_1$-$C_{12}$)-alkyl, —($C_6$-$C_{20}$)-aryl, —O—($C_6$-$C_{20}$)-aryl, —Cl,
where the alkyl and aryl groups mentioned may be substituted,
and at least one $R^{12}$, $R^{13}$, $R^{14}$, $R^{15}$, $R^{16}$, $R^{17}$, $R^{18}$ or $R^{19}$ radical is —H.

9. Method according to claim 7,
wherein the $R^1$, $R^2$, $R^3$, $R^4$, $R^5$, $R^{12}$, $R^{13}$, $R^{14}$, $R^{15}$, $R^{16}$, $R^{17}$, $R^{18}$, $R^{19}$ radicals are each independently selected from:
—H, —($C_1$-$C_{12}$)-alkyl, —O—($C_1$-$C_{12}$)-alkyl, —Cl,
where the alkyl groups mentioned may be substituted,
and at least one of the $R^1$ or $R^5$ or $R^2$ or $R^3$ radicals is —H,
and at least one of the $R^{12}$, $R^{13}$, $R^{14}$, $R^{15}$, $R^{16}$, $R^{17}$, $R^{18}$ or $R^{19}$ radicals is —H.

10. Method according to claim 7,
wherein the $R^1$, $R^2$, $R^3$, $R^4$, $R^5$, $R^{12}$, $R^{13}$, $R^{14}$, $R^{15}$, $R^{16}$, $R^{17}$, $R^{18}$, $R^{19}$, radicals are each independently selected from:
—H, —($C_1$-$C_{12}$)-alkyl, —O—($C_1$-$C_{12}$)-alkyl,
where the alkyl groups mentioned may be substituted,
and at least one of the $R^1$ or $R^5$ or $R^2$ or $R^3$ radicals is —H,
and at least one of the $R^{12}$, $R^{13}$, $R^{14}$, $R^{15}$, $R^{16}$, $R^{17}$, $R^{18}$ or $R^{19}$ radicals is —H.

11. Method according to claim 1 or 2,
wherein the monocyclic arene is a phenyl derivative and the bicyclic arene is a naphthyl derivative.

12. Method according to claim 1 or 2,
wherein one of the group of fluorinated alcohols, fluorinated carboxylic acids or organic carboxylic acids is added as solvent to the reaction mixture in method step d).

13. Method according to claim 1 or 2,
wherein 1,1,1,3,3,3-hexafluoro-2-propanol or trifluoroacetic acid is added as solvent.

14. Method according to claim 1 or 2,
wherein the selenium dioxide is added in a molar ratio based on the sum total of the phenol and the arene within a range from 0.1 to 2.0.

* * * * *

UNITED STATES PATENT AND TRADEMARK OFFICE
CERTIFICATE OF CORRECTION

PATENT NO. : 9,771,311 B2
APPLICATION NO. : 15/160367
DATED : September 26, 2017
INVENTOR(S) : Katrin Marie Dyballa et al.

It is certified that error appears in the above-identified patent and that said Letters Patent is hereby corrected as shown below:

In the Claims

Column 14, Claim 2, Line 27: replace "$R^{19}$" with --$R^{10}$--

Column 14, Claim 3, Line 33: at the end of the line following -O-($C_6$-$C_{20}$)-aryl, insert -- –Cl, --

Column 14, Claim 4, Line 44: at the end of the line following -($C_6$-$C_{20}$)-aryl, insert -- –Cl, --

Column 14, Claim 5, Line 52: at the end of the line following -O-($C_1$-$C_{12}$)-alkyl, insert -- –Cl, --

Column 15, Claim 7, Line 39: replace "$R^1$s" with --$R^{15}$--

Signed and Sealed this
Twenty-sixth Day of December, 2017

Joseph Matal
*Performing the Functions and Duties of the
Under Secretary of Commerce for Intellectual Property and
Director of the United States Patent and Trademark Office*